United States Patent [19]

Hernandez et al.

[11] Patent Number: 5,010,562

[45] Date of Patent: Apr. 23, 1991

[54] APPARATUS AND METHOD FOR INHIBITING THE GENERATION OF EXCESSIVE RADIATION

[75] Inventors: Francisco Hernandez, Concord; Jerry Chamberlain, Pittsburg, both of Calif.

[73] Assignee: Siemens Medical Laboratories, Inc., Walnut Creek, Calif.

[21] Appl. No.: 401,355

[22] Filed: Aug. 31, 1989

[51] Int. Cl.⁵ .................... A61N 5/10

[52] U.S. Cl. .................... 378/125; 378/126; 378/115; 250/492.3

[58] Field of Search .................... 250/492.3; 378/111-112, 114-119, 124-126, 143

[56] References Cited

U.S. PATENT DOCUMENTS

| | | | |
|---|---|---|---|
| 4,095,114 | 6/1978 | Taumann | 250/510 |
| 4,115,830 | 9/1978 | Stieber . | |
| 4,152,604 | 5/1979 | Burbury | 378/117 |
| 4,342,060 | 7/1982 | Gibson | 361/1 |
| 4,347,547 | 8/1982 | Gibson | 361/187 |
| 4,442,352 | 4/1984 | Brahme | 250/251 |
| 4,484,341 | 11/1984 | Luniewski | 378/69 |
| 4,627,089 | 12/1986 | Menor et al. | 378/157 |
| 4,726,046 | 2/1988 | Nunan | 378/65 |

*Primary Examiner*—Carolyn E. Fields
*Assistant Examiner*—David P. Porta
*Attorney, Agent, or Firm*—Lawrence C. Edelman

[57] ABSTRACT

The generation of excessive electron radiation or X-ray radiation is prevented in an apparatus which comprises an accelerator means for generating and accelerating electrons. These electrons form an electron beam which has a predetermined low intensity level for the generation of electron radiation or a predetermined high intensity level for the generation of X-ray radiation. In case of generating electron radiation a scattering foil or a target, respectively are arranged in the trajectory of the electron beam. The foil and the target are movably arranged on a support means. Detecting means operable by this support means sense the position of the foil and the target relative to the trajectory of said electron beam and inhibiting means prevent the generation of an electron beam having an intensity level which exceeds the predetermined low intensity level if the target is not positioned and/or which exceeds the predetermined high intensity level if the target is positioned in the trajectory of the electron beam.

19 Claims, 2 Drawing Sheets

APPARATUS AND METHOD FOR INHIBITING THE GENERATION OF EXCESSIVE RADIATION

CROSS-REFERENCE TO RELATED APPLICATION

This application is related to an application which is assigned to the same applicant as the present application and which was filed simultaneously with the present application and identified by U.S. patent application No. 07/401,605.

BACKGROUND OF THE INVENTION

1. Field of the Invention

This invention relates to a safety interlock system for an apparatus which generates either electron radiation or X-ray radiation. Such an apparatus is used e.g. for the medical treatment of patients.

2. Description of the Prior Art

It is known in the art of radiation systems to switch-off an unwanted radiation beam by utilizing an ionization chamber to which the radiation is applied, as soon as a previously determined dosage of radiation has been reached. U.S. Pat. No. 4,347,547 describes such a radiation system in which a linear accelerator emits electron pulses which are directed to a target for the generation of X-ray pulses. The ionization chamber is exposed to the X-ray pulses for measuring their intensity distribution. A discriminator is connected to the ionization chamber for detecting intensity inhomogeneities in the X-ray pulses. If the energy of the X-ray radiation is not between a predetermined maximum value and a predetermined minimum value, a switch is operated by the discriminator and switches off the accelerator by inhibiting the power supply of the accelerator. Simultaneously, there may also be stopped the high voltage supply to the accelerator, an RF voltage of a high frequency (HF) source and/or the injection of electrons into a waveguide of the accelerator.

U.S. Pat. No. 4,342,060 discloses another safety interlock system for a linear accelerator. A measuring device determines the level of the particle beam pulses emitted by the accelerator through a target which is exposed to the particle beam pulses. A discriminator determines whether the level of the particle pulses is higher than a predetermined value. If this is the case then a switch is operated which switches off the power supply of the accelerator, the RF signals of a HF power source and/or the emission of electrons of an electron gun of the accelerator.

From U.S. Pat. No. 4,115,830 a monitoring system for a high voltage supply of an ionization chamber is known. This system is preferably used for monitoring a particle accelerator in order to regulate the radiation intensity or the radiation output via the ionization current of the ionization chamber subjected to the radiation.

There have been known systems which are able to generate either electron radiation or X-ray radiation. In the case of generating electron radiation, a scattering foil is arranged at an exit window of the accelerator in the trajectory of the emitted electron beam. In case of generating X-ray radiation a target is arranged at the exit window of the accelerator in the trajectory of the electron beam and the particles emitted by the accelerator have high intensity so that they can generate enough bremsstrahlung for the generation of the X-rays. Such systems have been used e.g. for the medical treatment of patients with electron radiation or with X-ray radiation.

If a failure occurs during the operation of such a system and the particles having high intensity, like during the generation of X-ray radiation, are emitted by the accelerator and the scattering foil is positioned in the trajectory of the electron beam although the target should be in this position, the patient is exposed to a very high electron radiation and this could be very harmful to a patient.

If the radiation is measured by the ionization chamber according to the above noted prior art technique, there is still a certain risk that the patient receives too much radiation, because the accelerator is not switched-off, until after the radiation has left the accelerator and is measured and determined to be too great while already on its path to the patient.

SUMMARY OF THE INVENTION

1. Objects

It is an object of the invention to provide a safety interlock system which prevents an unwanted emission of high energy electron radiation and thus gives improved safety to the patient.

It is another object of the invention to provide a method for safely inhibiting the generation of high energy electron radiation if the target is not properly positioned in the trajectory of an electron beam having a high energy level.

2. Summary

According to the invention a safety interlock system for an apparatus which generates either electron radiation or X-ray radiation is provided which incorporates accelerator means for generating and accelerating electrons and emitting an electron beam formed by the electrons and having a predetermined low energy level for the generation of the electron radiation or a predetermined high energy level for the generation of said X-ray radiation. There is further provided a supporting means for movably supporting a scattering foil for generating the electron radiation upon impingement of the electron beam having the low intensity level and movably supporting a target for generating the X-ray radiation upon impingement of the electron beam having the high intensity level and for selectively moving one of the foil and the target into a predetermined position in the trajectory of the electron beam. A detecting means operable by movement of the supporting means senses the physical position of the target relative to the trajectory of the electron beam, and an inhibiting means coupled to the accelerator means and to the detecting means prevents the generation of an electron beam having an intensity level which exceeds the predetermined low intensity level if the target is not in said predetermined position in the trajectory of the electron beam.

The detecting means comprises a switch, preferably a mechanical switch, but it may also comprise a non-mechanical switch, such as an opto-electronic or magnetic switch.

The inhibiting means switches off the power supply of the accelerator if the target is not properly positioned in the trajectory of said electron beam, when the intensity of the electron beam exceeds the predetermined low energy level. Normally such an accelerator comprises an electron injector for emitting injector pulses, an electron gun for receiving these injector pulses and generating electrons, a waveguide for receiving these electrons and a high frequency (HF) source for generating RF signals for the acceleration of these electrons in the waveguide for generating the electron beam. In this case the inhibiting means preferably includes sensing means coupled to the electron injector for sensing the injector pulses and the inhibiting means disables the injector pulses and the RF signals if the target is not properly positioned in the trajectory of the electron beam when the intensity level of the electron level exceeds the predetermined low energy level. It is also possible to switch-off the high voltage of the accelerator, the RF signals generated by the HF source and/or the injection of the electrons into the waveguide.

According to the invention, in the method for preventing the generation of excessive electron radiation in an apparatus for generating either electron radiation upon impingement of an electron beam having a predetermined low intensity level on a scattering foil or X-ray radiation upon impingement of an electron beam having a predetermined high intensity level on a target the position of the target is sensed by a detecting means, and the generation of an electron beam having an intensity exceeding the predetermined low intensity level is prevented by an inhibiting means if the target is not properly positioned in the trajectory of the electron beam.

Additional features of the invention and additional objects of the invention will be more readily appreciated and better understood by reference to the following detailed description which should be considered in conjunction with the drawing.

DESCRIPTION OF THE PREFERRED EMBODIMENT OF THE INVENTION

Figure 1:
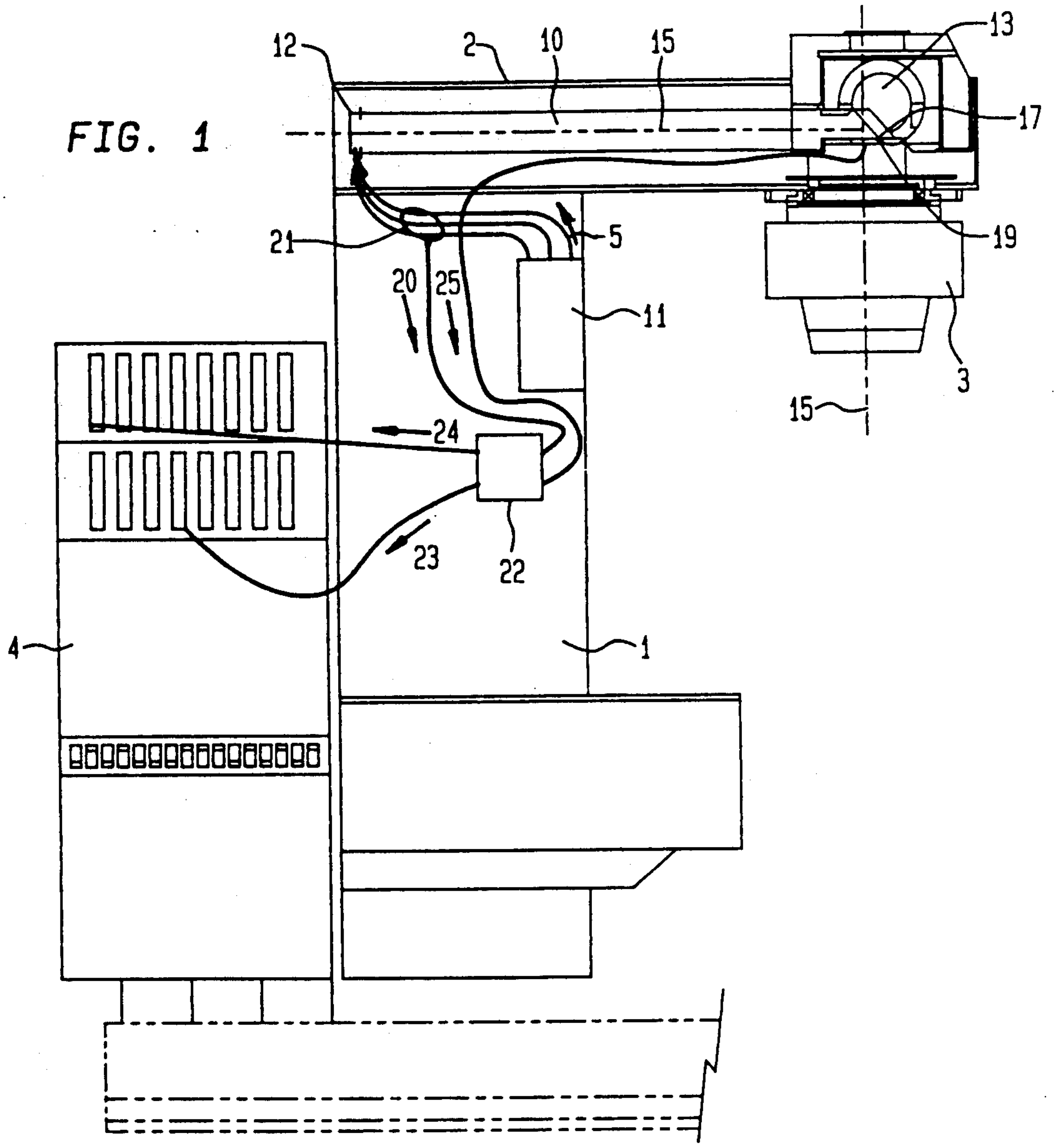
FIG. 1 depicts an apparatus for generating either X-ray radiation or electron radiation.

The apparatus shown in FIG. 1 is provided with an accelerator for the generation of either electron radiation or X-ray radiation and is for instance used for the medical treatment of a patient on a treatment table (not shown). A stand 1 supports a gantry 2 with a defining head 3. Next to stand 1 there is arranged a control unit 4 which includes control electronics for controlling different modes of operation of the apparatus. In stand 1 an electron injector 11 is provided which supplies injector pulses 5 to an electron gun 12 arranged in gantry 2. The electrons are emitted from electron gun 12 into an evacuated waveguide 10 for acceleration. For this purpose an HF source (not shown) is provided which supplies RF signals for the generation of an electromagnetic field supplied to waveguide 10. The electrons injected by injector 11 and emitted by electron gun 12 are accelerated by this electromagnetic field in waveguide 10 and exit waveguide 10 at the end opposite to electron gun 12 as an electron beam 15. Electron beam 15 then enters an evacuated envelope 13 which bends electron beam 15 by 270 degrees. Electron beam 15 then leaves envelope 13 through a window 17.

If electron radiation is to be generated, a scattering foil is moved into the trajectory of electron beam 15. If X-ray radiation is to be generated, a target is moved into the trajectory of electron beam 15 and the intensity level of electron beam 15 is caused to be higher than during the generation of the electron radiation. More intensity is necessary for generating X-ray radiation due to deceleration of the electrons in the target. The energy level of electron beam 15 is increased by correspondingly increasing the amplitudes of injector pulses 5 supplied by electron injector 11.

The scattering foil and the target (both shown in FIGS. 2 and 3) are arranged on a movable support means 19 which can be formed as a carriage or slide movably arranged under window 17. If X-ray radiation is to be generated, the target is moved into the trajectory of electron beam 15 and if electron radiation is to be generated the scattering foil is moved into the trajectory of electron beam 15. A detecting means (not shown in FIG. 1) senses the position of support means 19 and generates a position signal 25 which is responsive to the position of support means 19 and thus the position of the target and the scattering foil.

A sensing means 21 senses the amplitudes of injector pulses 5 supplied by electron injector 11 and generates a sensing signal 20 which corresponds to the amplitudes of injector pulses 5.

If the amplitude of an injector pulse 5 exceeds a reference voltage which is assigned to operation for the generation of electron radiation when the foil is in place or to the generation of X-ray radiation when the target is in place, then a switching unit 22 generates a safety interlock signal 23 which is applied to control unit 4 for immediately stopping the generation of electron beam 15.

In order to prevent the generation of the unwanted radiation as soon as possible, switching unit 22 also generates a disabling signal 24 which is also applied to control unit 4 for disabling the synchronization of injector pulses 5 and the RF signals in order to more quickly stop the radiation and minimize exposure of the patient to the unwanted radiation.

In defining head 3 there are provided at least one flattening filter for flattening the X-ray radiation emitted from the target and dose chambers (also called ionization chambers) for measuring the X-ray radiation and the electron radiation. In addition a collimator is provided in the trajectory of the radiation.

Figure 2:
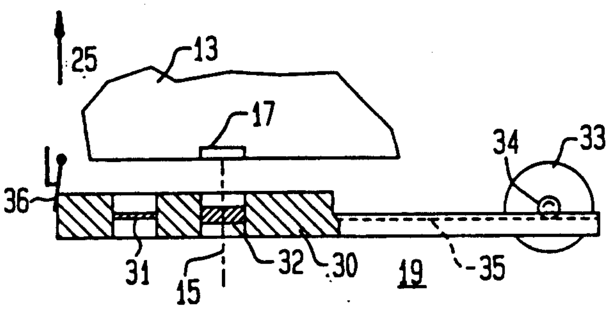
FIG. 2 shows a carriage supporting a scattering foil and a target in a first position for generating X-ray radiation.

FIG. 2 shows schematically the movable support means 19 which supports a scattering foil 31 for the generation of electron radiation and a target 32 for the generation of X-ray radiation. Support means 19 can also support further foils and/or targets in order to provide different types of electron or X-ray radiation and it can be formed as a carriage having small wheels or rollers. In the embodiment shown in FIG. 2, support means 19 is formed as a slide 30 and it is driven by an electric motor 33 through a tooth wheel 34 and a toothed rack 35 forming a rack and pinion drive. In FIG. 2 target 32 is shown properly positioned in the trajectory of electron beam 15 which is emitted through window 17 of envelope 13 for the generation of X-ray radiation. Detecting means 36 senses the position of slide 30 in order to determine whether the position of target 32 is proper. Detecting means 36 is formed as a mechanical switch, but it can also be formed as an opto-electronic or magnetic switch. When target 32 is properly positioned in the trajectory of electron beam 15, switch 36 is closed and position signal 25 is supplied to switching unit 22.

If the intensity level of electron beam 15 does not exceed a predetermined high value, then switching unit 22 neither generates safety interlock signal 23 nor disabling signal 24 and the accelerator means can generate an electron beam 15 having a high intensity level. By utilizing switch 36 it is guaranteed that a electron beam 15 having a high level can only be generated if target 32 for the generation of X-ray radiation is in its proper position. This means that the apparatus is extremely safe because no electron radiation of high intensity level can be generated if target 32 is not in its proper position. Even if target 32 is in its proper position it is still made sure that too high an intensity level is prevented from being emitted because switching unit 22 would generate safety interlock signal 23 and disabling signal 24 as soon as the energy of electron beam 15 exceeded the above mentioned predetermined high value assigned to the generation of X-ray radiation.

Figure 3:
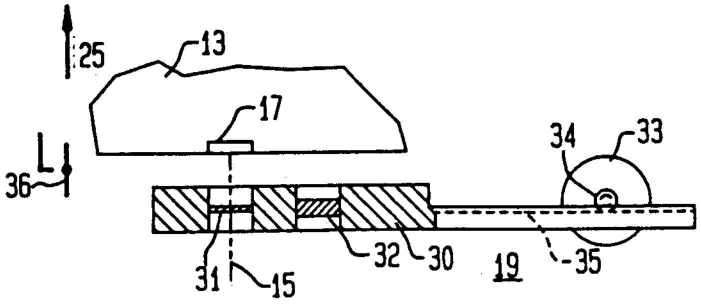
FIG. 3 shows the carriage according to FIG. 2 in a second position for generating electron radiation.

FIG. 3 shows the position of slide 30 if electron radiation is generated. In this case scattering foil 31 is positioned by motor 33 into the trajectory of electron beam 15. Switch 36 is now open and position signal 25 indicates to switching unit 22 that scattering foil 31 and not target 32 is in the trajectory of electron beam 15. Electron injector 11 now generates injector pulses 5 having low amplitudes in order to generate an electron beam 15 having a low intensity level. Switching unit 22 compares the amplitudes of injector pulses 5 sensed by sensing means 21 and transmitted to switching unit 22 by sensing signals 20 with a reference value assigned to the generation of electron radiation. If the amplitudes of injector pulses 5 do not exceed this reference value, the accelerator means starts generating an electron beam having a low energy level. If in case of defective operation injector 11 generated injector pulses 5 with high amplitude, like e.g. in case of generation of X-ray radiation, then switching unit 22 would immediately generate safety interlock signal 23 in order to switch-off the apparatus as soon as possible. Switching unit 22 would also generate disabling signal 24 in order to disable the injector pulses 5 and the RF signals. By these means it is guaranteed that the emission of electron radiation of high intensity from head 3 which could be hazardous to the patient3 s health, is minimized.

If there is provided a plurality of scattering foils and/or targets on slide 30, then a plurality of switches can be provided which are controlled e.g. by projections on slide 30 and which indicate to switching unit 22 whether a foil or a target is properly positioned in the trajectory of electron beam 15.

Figure 4:
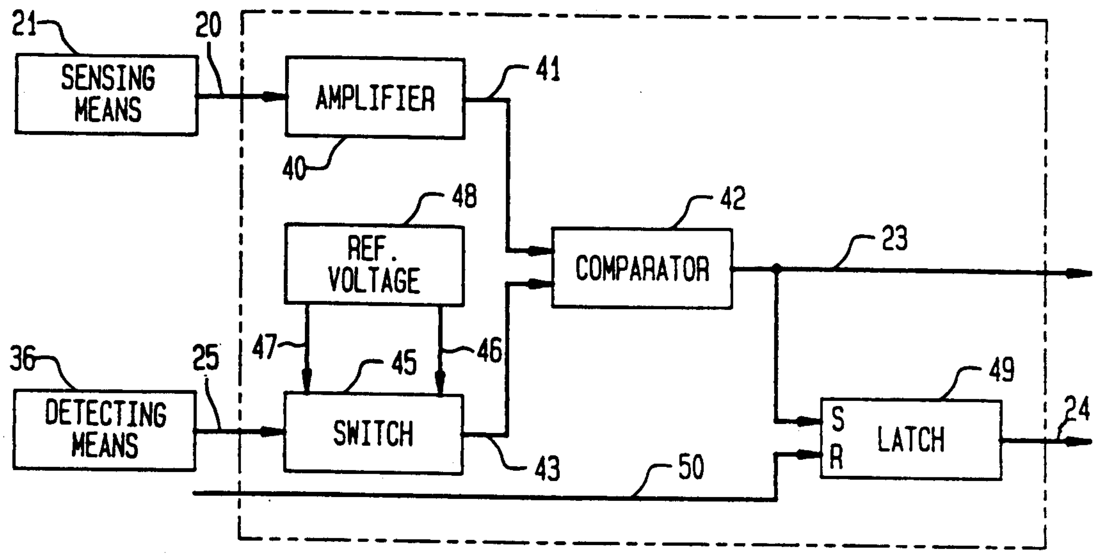
FIG. 4 shows a block diagram of a safety interlock circuit for inhibiting the generation of unwanted radiation.

FIG. 4 depicts a block diagram of switching unit 22 for generating safety interlock signal 23 and/or disabling signal 24. Sensing means 21, preferably formed as a current transformer, senses injector pulses 5 and supplies sensing signals 20 through an amplifier 40 as amplified sensing signals 41 to a comparator 42. Comparator 42 compares the amplitudes of amplified sensing signals 41 with a reference voltage 43. Reference voltage 43 is supplied from a switch 45 which is formed as an analog switch and which is operated by position signal 25 generated from switch 36. Switch 36 switches either a first reference voltage 46 assigned to the generation of X-ray radiation and having a high voltage value or a second reference voltage 47 assigned to the generation of electron radiation and having a low voltage value to comparator 42. Reference voltages 46 and 47 are generated in reference voltage source 48.

If the apparatus is set to operate for X-ray radiation and position signal 25 indicates that target 32 is in the proper position in the trajectory of electron beam 15, then high reference voltage 46 is supplied through switch 45 to comparator 42. If then an operator sets a control panel of the apparatus to operate for the generation of X-ray radiation, injector 11 generates injector pulses 5 having high amplitudes. Sensing means 21 sense injector pulses 5 and supply sensing signals 20 through amplifier 40 to comparator 42. Comparator 42 compares the amplitudes of amplified sensing signals 41 with the first reference voltage 46. As long as the amplitudes of amplified sensing signals 41 do not exceed this first reference voltage 46, the accelerator generates the electron beam having the high intensity level and the apparatus generates the X-ray radiation. But as soon as the amplitude of an amplified sensing signal 41 exceeds this first reference voltage 46, comparator 42 generates safety interlock signal 23 which prevents any further generation of radiation. Safety interlock signal 23 is fed to the set input S of a latch 49 and puts it in its sets position. At the output of latch 49 disabling signal 24 is supplied to the trigger for the generation of injector pulses 5 and the RF signals. Latch 49 is reset by a signal 50 supplied to the reset input R of latch 49. Signal 50 is generated by control unit 4 only after the radiation has been switched off. Thus, the generation of X-ray radiation can only be continued if the apparatus is restarted from the beginning again.

In case of generating electron radiation, motor 33 moves scattering foil 31 into the proper position in the trajectory of electron beam 15 and injector 11 generates injector pulses 5 having a low amplitude in order to generate an electron beam 15 having a low intensity level. When foil 31 is in its proper position switch 36 is open and generates a corresponding position signal 25. This position signal 25 operates switch 45 so that low reference voltage 47 is supplied as reference voltage 43 to comparator 42. As long as amplified sensing signals 41 have an amplitude which is smaller than reference voltage 43, then neither a safety interlock signal 23 nor a disabling signal 24 is generated. But, if in case of e.g. a component failure, the amplitude of amplified sensing signals 41 exceed reference voltage 43, then immediately afterwards safety interlock signal 23 and disabling signal 24 will be generated in order to prevent emission of any unwanted radiation.

It is extremely important that in case of operation when foil 31 is in the trajectory of electron beam 15, that the accelerator only generates only an electron beam 15 having low intensity level, because otherwise the patient could be exposed to hazardous radiation. If, in the case of failure, the accelerator generated e.g. an electron beam 15 having a high intensity level like e.g. for the generation of X-ray radiation and foil 31 was in the trajectory of electron beam 15 instead of target 32, then a far too high electron radiation would be emitted. But by the utilization of switch 36 according to the invention the emission of such radiation is safely prevented.

Switch 45 can also be switched by signals which are different from position signal 25 or which are a combination of position signal 25 and such signals. Such signals are e.g. signals which indicate that the correct flattening filter and/or the correct dose chamber is in the correct position in the trajectory of electron radiation or X-ray radiation. The generation of such signals is generally known in the art. It is further possible to change the position of switch 45 by a signal which is generated by an operator if he selects between a generation of electron radiation and X-ray radiation.

Figure 5:
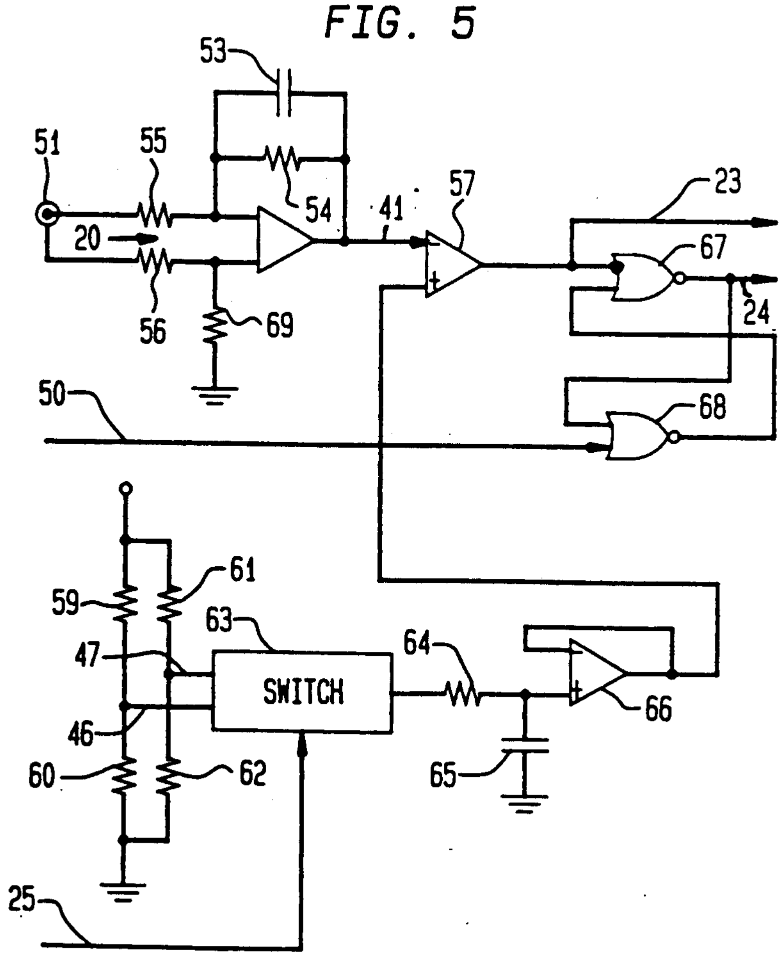
FIG. 5 depicts a circuit diagram of the safety interlock circuit of FIG. 4.

The circuit diagram depicted in FIG. 5 shows details of switching unit 22 illustrated in FIG. 4. Sensing signals 20 are fed through a conventional BNC connector 51 and through resistors 55 and 56 to amplifier 40 which comprises a differential amplifier 52 having a capacitor 53 and a resistor 54 in his feedback path. Another resistor 69 connects the non-inverting input of amplifier 52 to ground. Amplifier 52 amplifies sensing signals 20 by approximately the factor 6.7 and provides the amplified sensing signal 41 to the inverting input of a fast comparator 57 which forms comparator 42. Such a fast comparator 57 is commercially available as an integrated circuit under the name LM 311.

Position signal 25, which senses the position of slide 30 and thus the position of foil 31 and target 32, is supplied to the gate of analog switch 63 forming switch 45 together with an amplifier 66 and a low pass filter comprising a resistor 64 and a capacitor 65. Analog switch 63 is formed as an integrated circuit and is commercially available under the name AD 7512.

A negative position signal 25 of about −2V indicates that the target 32 is in place and a positive position signal 25 of about +5V and indicates that foil 31 is in place. Analog switch 63 selects between the two reference voltages 46 and 47 supplied by reference voltage source 48. Reference voltage source 48 comprises two voltage dividers formed of two pairs of resistors 59, 60 and 61, 62, respectively. Reference voltage 46 is approximately +9 V and represents a maximum amplitude of injector pulses 5 of approximately 1.3 A for the generation of X-ray radiation. reference voltage 47 is approximately +1.3 V and represents a maximum amplitude of injector pulses 5 of approximately 180 mA. The output of switch 63 is coupled through the low pass filter and amplifier 66 to the non-inverting input of comparator 57.

Whenever the amplitude of amplified sensing signal 41 is higher than the selected reference voltage 43, the output of comparator 57 is low and the safety interlock signal 23 is active and latched in flip-flop 49 which is formed of two cross connected NOR-gates 67 and 68, wherein inverted safety interlock signal 23 is supplied to the input of NOR-gate 67. Safety interlock signal 23 is active if injector pulses 5 with an amplitude of more than 180 mA are injected in electron gun 12 when electron foil 31 is in the path of electron beam 15, or if injector pulses 5 with amplitudes of more than 1.3 A are injected in electron gun 12 when target 32 is in place.

Flip-flop 49 can only be reset by reset signal 50 after the radiation has been switched off either automatically or by an operator. In this case signal 50 is generated and supplied to an input of NOR-gate 68 in order to reset flip-flop 49.

There has been shown and described a novel apparatus and method for preventing the generation of excessive radiation which fulfills all the objects and advantages sought therefor. Many changes, modifications, variations and other uses and applications of the subject invention will, however, become apparent to those skilled in the art after considering the specification and the accompanying drawings which disclose an embodiment thereof. All such changes, modifications, variations and other uses and applications which do not depart from the spirit and scope of the invention are deemed to be covered by the invention which is limited only by the claims which follow.

We claim:

1. An apparatus for generating electron radiation or X-ray radiation, said apparatus comprising:
   - accelerator means for generating and accelerating electrons to form an electron beam which has a predetermined low intensity level for the generation of said electron radiation or a predetermined high intensity level for the generation of said X-ray radiation;
   - supporting means for supporting a scattering foil and a target and for selectively moving either said foil into the trajectory of said electron beam having said low intensity level for generating said electron radiation upon impingement of said electrons there or on said target into the trajectory of said electron beam having said high intensity level for generating said X-ray radiation upon impingement of said electrons thereon;
   - detecting means operable by said supporting means for sensing the position of said target relative to the trajectory of said electron beam; and
   - inhibiting means coupled to said accelerator means and to said detecting means for preventing the generation of an electron beam having said high intensity level if said foil and not said target is positioned in the trajectory of said electron beam.

2. An apparatus according to claim 1, wherein said inhibiting means prevents the generation of an electron beam having an intensity level which exceeds said predetermined low intensity level if said foil is positioned in the trajectory of said electron beam.

3. An apparatus according to claim 1, wherein said inhibiting means prevents the generation of an electron beam having an intensity level which exceeds said predetermined high intensity level if said target is positioned in the trajectory of said electron beam.

4. An apparatus according to claim 1, wherein said accelerator means includes a power supply and said inhibiting means switches off said power supply if said target is not positioned in the trajectory of said electron beam and if the intensity of said electron beam exceeds said predetermined low intensity level.

5. An apparatus according to claim 1, wherein said detecting means is formed of a mechanical switch.

6. An apparatus according to claim 1, wherein said accelerator includes an electron injector for emitting injector pulses, an electron gun for receiving said injector pulses and generating electrons, a waveguide for receiving said electrons and a HF source for generating RF signals for the acceleration of said electrons in said waveguide for generating said electron beam, wherein said inhibiting means includes sensing means coupled to said electron injector for sensing the amplitudes of said injector pulses and wherein said inhibiting means prevents the generation of an electron beam having an intensity level which exceeds said predetermined low intensity level if said target is not positioned in the trajectory of said electron beam and if the amplitudes of the sensed injector pulses exceed a predetermined value assigned to said predetermined low intensity level.

7. An apparatus according to claim 6, wherein said inhibiting means prevents the generation of an electron beam by disabling said injector pulses and said RF signals.

8. An apparatus according to claim 6, wherein said inhibiting means includes a comparator coupled to said sensing means and to a reference voltage source which supplies a first reference voltage assigned to said predetermined low intensity level and wherein said comparator compares the injector pulses sensed by said sensing means with said first reference voltage and supplies a disabling signal to said accelerator for preventing the generation of said electron beam if the target is not positioned in the trajectory of said electron beam and if said sensed injector pulses exceed said first reference voltage.

9. An apparatus according to claim 8, wherein said reference voltage source supplies said first reference voltage assigned to said predetermined low intensity level and a second reference voltage assigned to said predetermined high intensity level comparator, wherein said reference voltage source is coupled to said comparator via a switch, which is controlled by said detecting means and which switches said first or said second reference voltage to said comparator if said target is not or is, respectively properly positioned in the trajectory of said electron beam.

10. An apparatus according to claim 9, wherein said switch is formed as an analog switch.

11. An apparatus according to claim 6, wherein an amplifier is arranged between said sensing means and said comparator.

12. An apparatus according to claim 6, wherein said inhibiting means comprises latching means, a set input of which is coupled to said comparator, a reset input of which is coupled to a switch supplying a signal if the radiation is switched off and an output of which is coupled to said accelerator means.

13. An apparatus according to claim 1, wherein said supporting means is formed as a slide which is movable by an electric motor.

14. An apparatus according to claim 6, wherein said sensing means is formed as a current coil for sensing said injector pulses.

15. A method for preventing the generation of excessive electron radiation in an apparatus for generating either electron radiation upon impingement of an electron beam having a predetermined low intensity level on a properly positioned scattering foil or X-ray radiation upon impingement of an electron beam having a predetermined high intensity level on a properly positioned target, said method comprising the steps of:

sensing the position of said target with a sensor included in the apparatus, and inhibiting the generation of said electron beam having said predetermined high intensity level if the target is not properly positioned in the trajectory of said electron beam.

16. A method according to claim 15, wherein the generation of an electron beam having an intensity level exceeding said predetermined high intensity level is prevented if the target is positioned in the trajectory of said electron beam.

17. A method according to claim 15, wherein the electron beam is generated by injecting injector pulses into an electron gun and accelerating electrons which are emitted by said electron gun in a wave guide by an electric field which is generated by RF signals generated in a HF source and wherein the generation of said electron beam is prevented by inhibiting said injector pulses and said HF signals.

18. A method according to claim 17, wherein the intensity level of said electron beam is measured by sensing the amplitudes of said injector pulses.

19. A method according to claim 18, wherein the amplitudes of said sensed injector pulses are compared to predetermined reference voltages assigned to said predetermined intensity levels.

* * * * *